United States Patent
DeLange et al.

(10) Patent No.: US 7,135,833 B2
(45) Date of Patent: Nov. 14, 2006

(54) MOTOR CONTROL FOR FLUX-REDUCED BRAKING

(75) Inventors: Robert J. DeLange, Greenfield, WI (US); Timothy M. Rowan, Wauwatosa, WI (US)

(73) Assignee: Rockwell Automation Technologies, Inc., Mayfield Heights, OH (US)

(*) Notice: Subject to any disclaimer, the term of this patent is extended or adjusted under 35 U.S.C. 154(b) by 0 days.

(21) Appl. No.: 11/261,352

(22) Filed: Oct. 28, 2005

(65) Prior Publication Data

US 2006/0113929 A1     Jun. 1, 2006

Related U.S. Application Data

(63) Continuation of application No. 11/002,012, filed on Nov. 30, 2004, now abandoned.

(51) Int. Cl.
*H02P 3/18* (2006.01)

(52) U.S. Cl. .................. 318/762; 318/760; 318/763; 318/744; 318/727

(58) Field of Classification Search ................ 318/762, 318/760, 727, 744, 763
See application file for complete search history.

(56) References Cited

U.S. PATENT DOCUMENTS

| | | | | |
|---|---|---|---|---|
| 3,859,579 | A * | 1/1975 | Plunkett | 318/805 |
| 4,524,316 | A * | 6/1985 | Brown et al. | 318/809 |
| 5,070,290 | A * | 12/1991 | Iwasa et al. | 318/758 |
| 6,229,278 | B1 * | 5/2001 | Garces et al. | 318/801 |
| 6,262,555 | B1 * | 7/2001 | Hammond et al. | 318/759 |
| 6,373,204 | B1 * | 4/2002 | Peterson et al. | 318/41 |
| 6,417,644 | B1 * | 7/2002 | Hammond et al. | 318/759 |
| 6,429,612 | B1 * | 8/2002 | Kume et al. | 318/139 |
| 6,768,284 | B1 * | 7/2004 | Lee et al. | 318/808 |

* cited by examiner

*Primary Examiner*—Rita Leykin
(74) *Attorney, Agent, or Firm*—Quarles & Brady LLP; William R. Walbrun

(57) ABSTRACT

A method and apparatus for braking an AC motor in the higher portion of its speed range includes substantially reducing flux before applying reverse torque commands to brake the motor. A DC link bus regulator is employed to prevent increases in bus voltage and frequency.

23 Claims, 6 Drawing Sheets

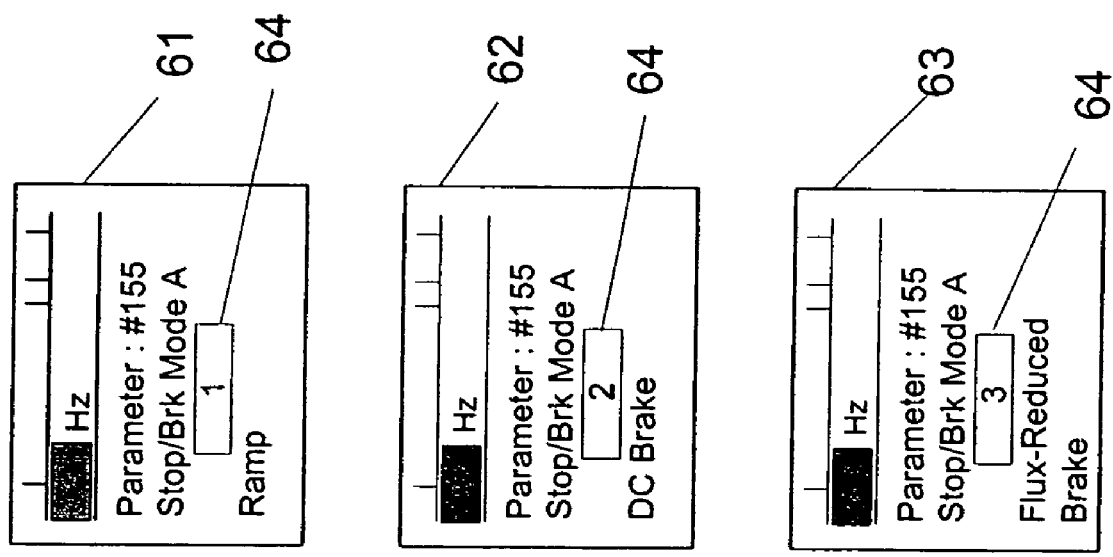

MOTOR CONTROL FOR FLUX-REDUCED BRAKING

CROSS-REFERENCE TO RELATED APPLICATIONS

This patent application is a continuation of U.S. patent application Ser. No. 11/002,012 which was filed on Nov. 30, 2004 now abandoned and which is entitled "MOTOR CONTROL FOR FLUX-REDUCED BRAKING".

STATEMENT REGARDING FEDERALLY SPONSORED RESEARCH

Not applicable.

TECHNICAL FIELD

The field of the invention is control systems for controlling the operation of AC motors.

BACKGROUND ART

Various methods have been known for braking of AC motors. One common method is to supply DC current (zero frequency current) to the motor. This produces a stationary magnetic field in the motor air gap to oppose rotation. When the spinning rotor interacts with this field, it produces negative braking torque. Such an approach is sometimes called "DC braking," or "DC injection braking." In drives (motor controls) where the control functions are performed by a microprocessor executing a stored program of instructions, DC injection adds no additional components and adds little to the cost of the basic drive. However, at high speeds, such as near or above base speed, the available torque may not be as high as desired to bring the motor speed down quickly.

In motors run by inverters with the capacity for operation in a regenerating mode, it is possible to use reverse power flow to provide a negative torque on the spinning rotor. Regenerative braking, using resistors, requires a high current switch which may comprise semiconductors and a resistor of sufficient size to absorb the generated heat.

Steicher, U.S. Pat. No. 6,577,483, illustrates a dynamic braking method where power is returned to the DC bus using a switching brake controller and a power resistor to dissipate power in the form of heat as power is returned to the DC bus during braking.

More recently, there has been interest in dual frequency braking methods. As disclosed in Hammond et al., U.S. Pat. No. 6,262,555, and U.S. Pat. No. 6,417,644, a converter supplies variable frequency AC power to the motor. A first frequency is supplied for normal motoring operation and is summed with a second frequency, a loss-inducing frequency, which is provided when it is desired to produce braking torque. The level of braking can be controlled to generally consume some or all of the braking in the device or motor. As a result of applying these two frequencies simultaneously, further actions must be taken to limit motor pulsation.

Another variable frequency technique is disclosed in U.S. Pat. No. 6,429,612. In this method, using a V/F controller without a current regulation loop, the frequency is reduced by two-thirds from rated operating frequency at synchronous speed and is then again reduced by two-thirds in a second step. This is said to ramp down the speed of the motor while limiting power feedback to that which can be dissipated in the rotor.

The prior art provides braking with relatively high flux remaining in the motor. This can result in tripping of current limit devices. The present invention is aimed at achieving a better control of the braking operation from higher speeds.

The present invention is also aimed at providing the user with a selection of the various types of braking, including several types discussed above.

SUMMARY OF THE INVENTION

The invention relates a method and apparatus for braking an AC motor, in which flux in the motor is reduced to near zero and upon reaching the flux-reduced state, sensing dc bus voltage to provide a feedback signal to the DC bus regulator that adjusts the frequency of the current as a function of dc bus voltage to provide continuous control of frequency down to 3 Hz; and also upon reaching the flux-reduced state, providing the motor current regulation loop with current commands that provide braking torque to the motor.

The invention provides a smooth speed deceleration profile based on a frequency reduction profile provided by the DC bus regulator as braking torque is applied without causing significant power regeneration.

The invention allows this form of braking to be achieved without adding circuitry and its resulting cost. The invention is executed primarily under program control of a microelectronic processor which receives feedback signals from the motor buses.

The invention also allows the user to select this form of braking from among two other forms of braking, dc braking and dynamic breaking.

The invention provides a further mode of shut-off braking once the drive has reached a low speed or in the event that it attempts to speed up again.

These and other objects and advantages of the invention will be apparent from the description that follows and from the drawings which illustrate embodiments of the invention, and which are incorporated herein by reference.

BRIEF DESCRIPTION OF THE DRAWINGS

FIG. 4 is a detail view of the setting of operating parameters to invoke the method of FIG. 2 in the controller of FIG. 1;

DETAILED DESCRIPTION OF THE PREFERRED EMBODIMENTS

Figure 1:
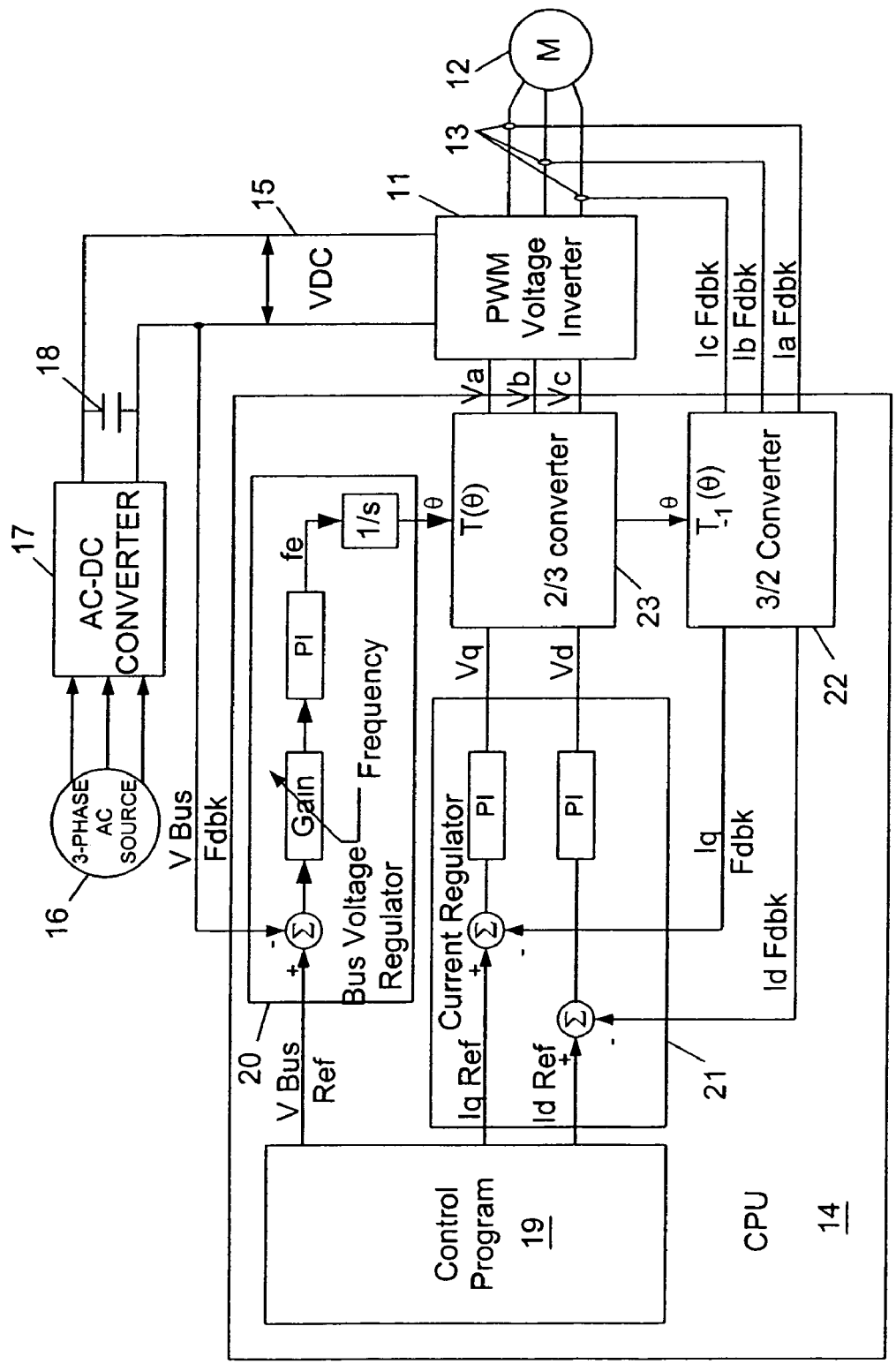
FIG. 1 is a block diagram of a motor drive for practicing the method of the present invention.

FIG. 1 illustrates a block diagram of a motor control processor 10 in a motor drive for practicing the present invention. The motor control processor 14 is connected to supply three phase voltage signals, Va, Vb and Vc to a PWM voltage inverter 11 in the motor drive, which in turn supplies current to an AC motor 12. Current feedback devices 13 are placed in the lines going to the motor 12 and provide current feedback signals, $I_{a\ Fdbk}$, $I_b$ Fdbk and $I_c$ Fdbk to the motor control CPU 14. The motor control CPU 14 is preferably a microelectronic CPU operating according to instructions in a stored control program 19. The program includes instructions for performing regulation of a DC bus voltage and regulation of current supplied to the motor 12.

The PWM inverter 11 receive power from a DC bus 15, which receives power from an AC source 16 that is rectified by rectifier 17 to provide DC voltage on the DC bus 15. A capacitor 18 (here specify function of the capacitor.)

Execution of the control program 14 results in a nominal DC bus reference value ($V_{Bus}$ Ref), which is one input to the DC Bus Regulator loop 20. A DC bus feedback voltage ($V_{Bus}$ Fdbk) sensed from the DC bus 15 by an appropriate sensor is algebraically summed (in this case, subtracted) from this nominal DC bus reference value. The result is multiplied by an adjustable gain function (GAIN) and processed through a proportional-integral (PI) loop of a type well known in the art to produce a frequency command ($f_e$). This frequency command ($f_e$) is integrated, as represented by the "1/s" function to provide a reference angle command (θ) for a motor controlled in the d-q synchronous reference frame, where current and voltage commands are resolved along a d-axis and a q-axis and where the conversions from 2-phase to 3-phase and from 3-phase to 2-phase represent vector multiplications by sin θ and cos θ. For further information on reference frame theory, reference is made to U.S. Pat. No. 5,140,248, assigned to the assignee of the present invention.

Although the current regulator shown in FIG. 1, is a synchronous current regulator, the present invention could be practiced with several other ways to regulate current. For example, the current regulator could operate in the stationary reference frame, or it could be operated by using the magnitude of current.

The execution of the control program 19 also provides a Current Regulator loop 21 in which current commands in the d-q synchronous reference frame, $I_q$ Ref and $I_d$ Ref are algebraically summed (actually, by subtracting) feedback signals $I_q$ Fdbk and $I_d$ Fdbk, which are the result of processing feedback signals, $I_{a\ Fdbk}$, $I_b$ Fdbk and $I_c$ Fdbk through a 3-phase to 2-phase converter 22. This produces two differences that are processed through respective PI (proportional-integrator) control loops to produce, $V_q$ and $V_d$ commands to a 2-phase to 3-phase converter 23. This converter also receives the reference angle command (θ) and together with the $V_q$ and $V_d$ commands, produces the phase voltage outputs $V_a$, $V_b$ and $V_c$ to the PWM inverter 11.

The present invention assumes the motor 12 is being operated at some forward motoring speed. At base speed, the motor 12 would operate at a rated frequency of 60 Hz. Above base speed the frequency could increase with speed up to as high as 90 Hz and even higher provided the inverter could supply the frequency. Below base speed, the frequency could be lower than 60 Hz. According to the invention, if it is now desired to stop the motor, a program routine represented by the flow chart in FIG. 2 is executed.

Figure 2:
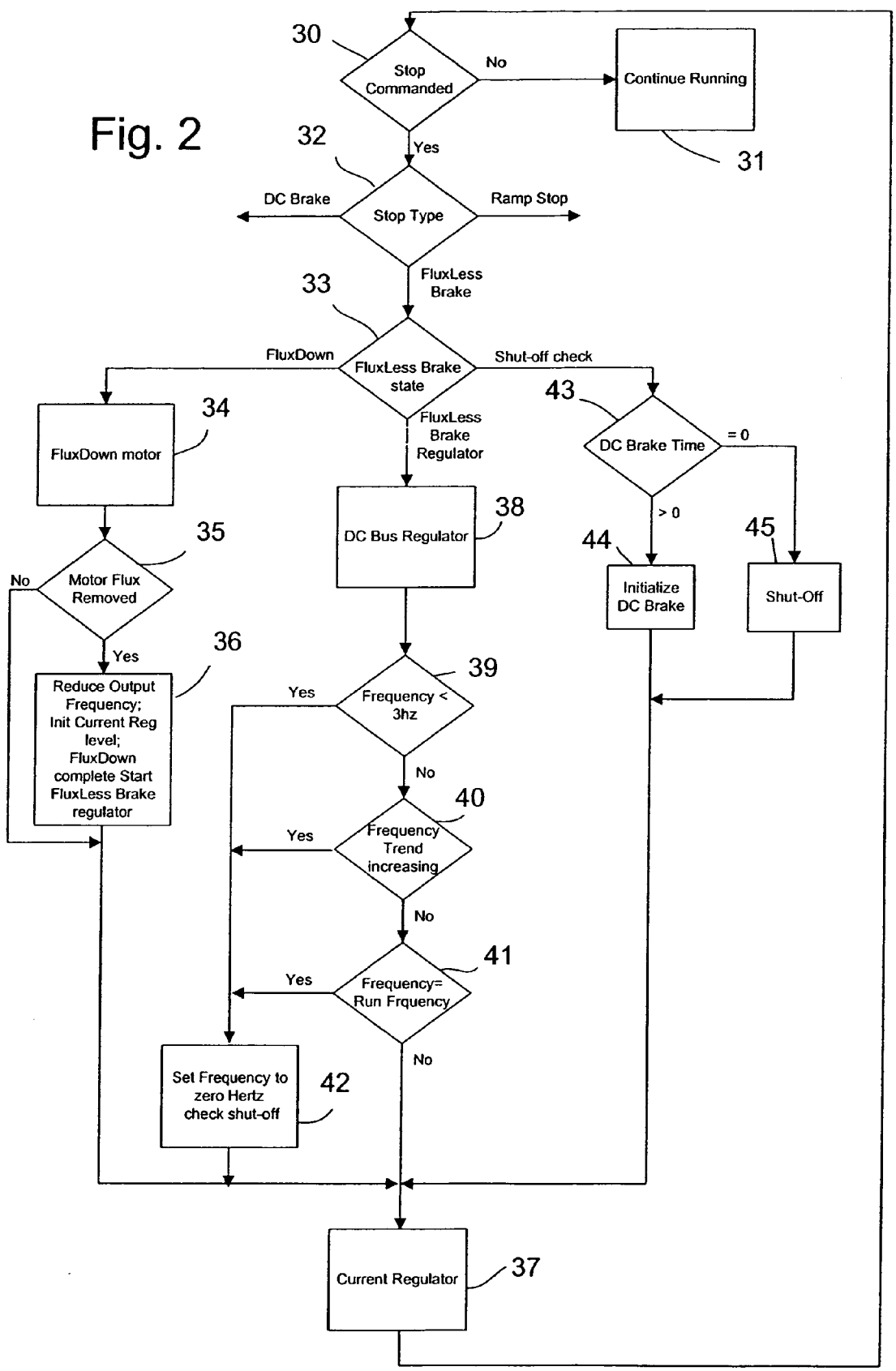
FIG. 2 is a flow chart of a routing in a control program for controlling operation of the motor drive of FIG. 1.

Referring to FIG. 2, the entry into the routine is represented by decision block 30, which is executed to check for a stop command through a user-operable push button or other suitable control. If the result of this test is negative, as represented by the "No" result, then the program returns to a "run mode" represented by process block 31. If the result of this test is positive, as represented by the "Yes" result, then the program proceeds to executes an instruction represented by decision block 32 to determine which type of stopping has been selected by a user. As explained in more detail below, the user can select from among the stopping method of the present invention, or dc braking or dynamic braking, the latter two methods being described in the background section herein. Assuming that the method of the invention has been selected then the program proceeds to executes an instruction represented by decision block 33 to determine whether the level of flux in the motor has been reduced. If the level of flux has not yet been reduced, then the routine proceeds to a flux down process represented by process block 34.

Figure 6:
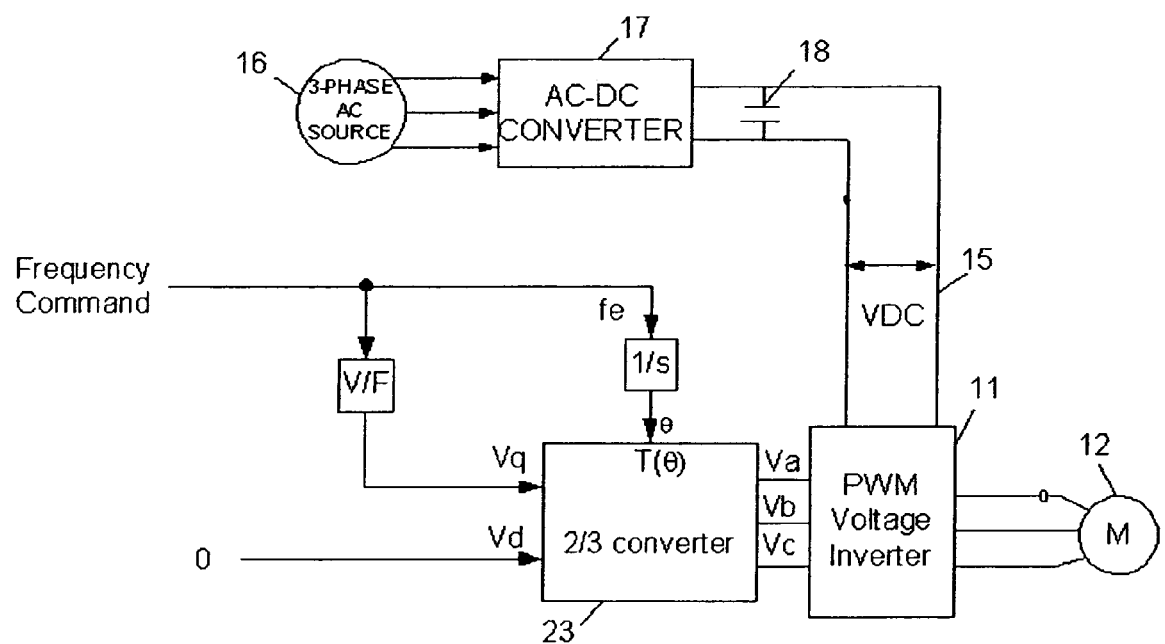
FIG. 6 is a detail diagram of the motor drive operation during a flux-down step in the control method.

During the flux-down process the motor control functions as seen in FIG. 6. The current regulator and dc bus regulator loops shown in FIG. 1 only relate to the actual braking process, which takes place after the flux-down has been completed.

As seen in FIG. 6, a conventional Volts-per-Hertz type control is executed during normal running (before flux-down and subsequent braking). The frequency (fe) command comes from the frequency reference (the speed command for the motor) and the voltage command (V) comes from a value proportional to the frequency command. When stopping is initiated, flux-down occurs. This is accomplished by holding the frequency at its last running value and then reducing the q-axis voltage command (Vq) to near zero as fast as possible without the motor current going too high. When the voltage gets near zero, flux-down is considered complete.

With this explanation, please refer back to FIG. 2 where decision block 35 is then executed to check for completion of this flux-down step. Upon reaching the flux-reduced state, the output frequency is reduced by an amount in a range from 40% to 57%. For example, if the motor were running at 60 Hz, frequency would be reduced to about 30 Hz. If the motor were operating at 90 Hz, the frequency would be reduced to about 45 Hz. Upon reaching the flux-reduced state, the motor Current Regulator loop 21 is also provided with initial current commands that provide braking torque to the motor. The initial changes in frequency and current commands are represented by process block 36. The routine will then proceed to activate the motor Current Regulator loop 21 as represented by process block 37. At that point the routine will loop back to the decision block 30 and start over. One pass through the routine will be completed in a predetermined interrupt cycle time.

After many cycles through the routine, the level of flux in the motor determined in decision block 33 will have been reduced and the routine will activate the DC bus regulator (block 38) designed to continuously adjust the frequency as a function of dc bus voltage and allow maximum braking torque while preventing power regeneration back into the dc bus and subsequent bus over voltage faults.

The frequency generated by block 38 may initially increase if the original frequency step from block 36 was too large, but the frequency will eventually decrease as the DC bus regulator brings the motor to a final stop. The control will continue to loop through the process, running the DC bus regulator and the current regulator until any one of the following three conditions occur:

1) the frequency command drops below 3 Hz;
2) a frequency trend shows an increase instead of a decrease; or
3) the frequency command reaching the flux-reduced operating frequency.

The conditions are tested for as represented by decision blocks 39, 40 and 41. If any of these tests is positive, the frequency is set to zero and a check will be made the next time through the routine for complete shut-off as represented by process block 42.

The next time that decision block 33 is reached, the shut-off state will be active and the routine will branch to a DC braking routine represented by timing check block 43 and two timing process blocks 44, 45 in which DC is applied to completely stop the motor.

Figure 3:
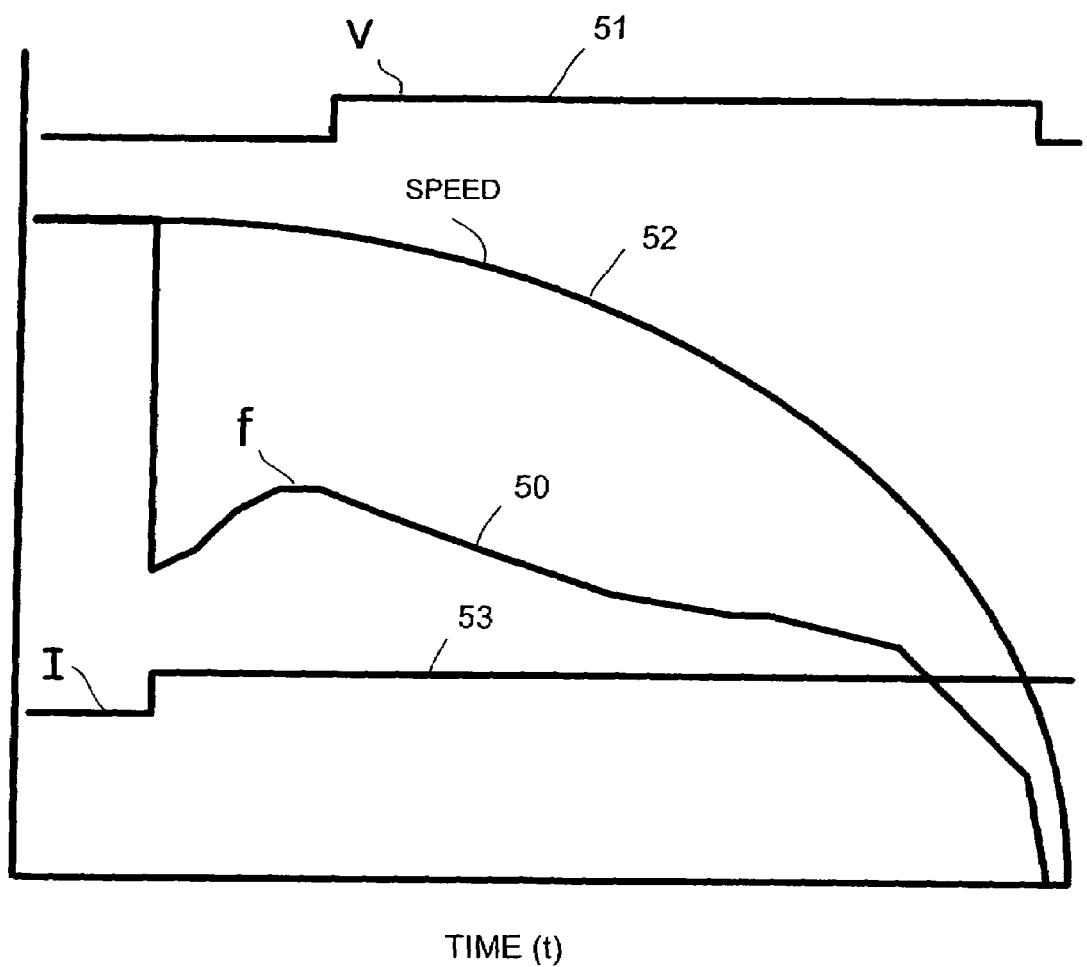
FIG. 3 is a graph of several operating parameters of the motor seen in FIG. 1.

The advantageous operation of the present invention is further illustrated in the curves in FIG. 3. After flux-down is completed, the sharp decrease in output frequency (f) 50 can be seen. At the same time, the current (I) 53 is increased to apply braking torque.

Since the initial frequency reduction was too large, the DC bus voltage (V) 51 is below its nominal DC bus reference value, causing DC bus regulator to increase the output frequency (f) 50. Eventually the DC bus voltage (V) 51 rises, causing the DC bus regulator to decrease the output frequency (f) 50. The decreasing operating frequency will cause the speed 52 of the motor to follow an increasingly downward sloping curve (as opposed to a ramp function) to zero.

FIG. 4 illustrates a screen display on a personal computer used to configure the motor drive control in which three instances 61, 62 and 63 of a data dialog box are shown, representing regenerative ramp braking, dc braking and the flux-down braking of the present invention. This is user-selectable parameter #155. If a "1" is inserted in the data entry location, then regenerative ramp braking is selected. If a "2" is inserted in the data entry location, then dc braking is selected. If a "3" is inserted in the data entry location 64, then flux-down braking is selected. This parameter or a corresponding value is stored in memory for access by the CPU 14 to carry out the selected mode of braking.

Figure 5A:
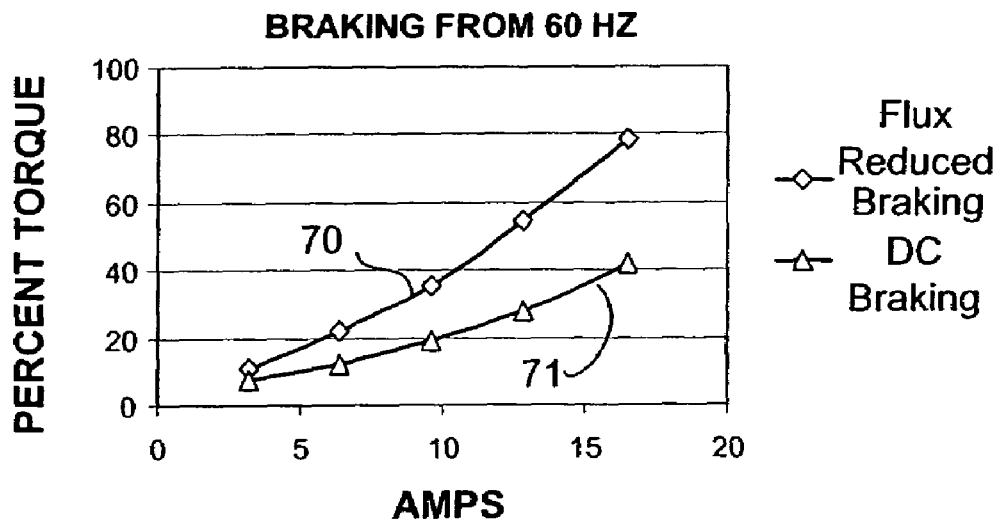
FIGS. 5a and 5b are graphs of the braking torque produced by the present invention in comparison with other known methods.
Figure 5B:
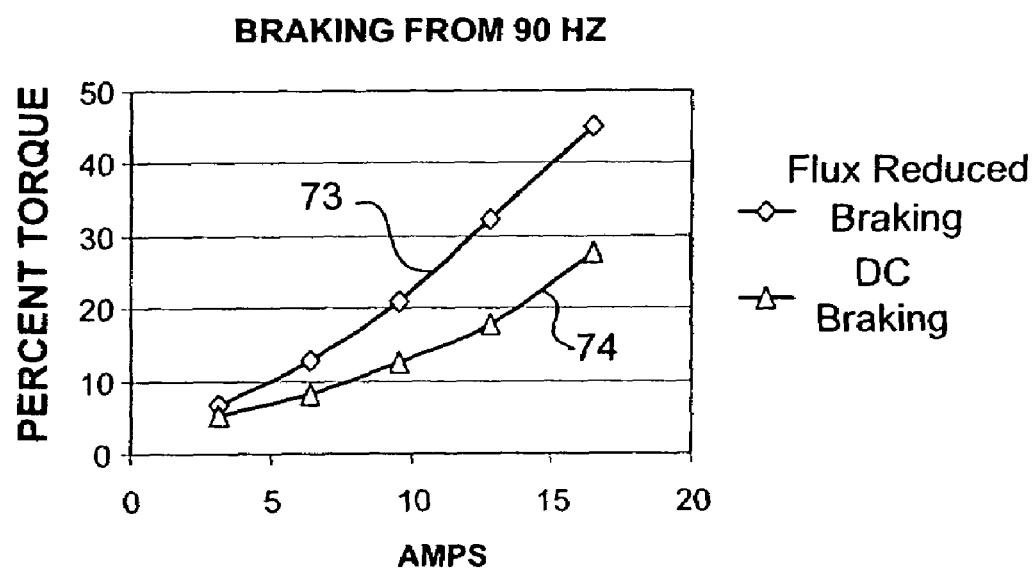

FIGS. 5a and 5b illustrate a curve 70 for the higher braking torque available with the present invention as compared with a curve 71 for dc braking as taught in the prior art. FIG. 5a shows this result for a 5 HP motor braked from a speed corresponding to a frequency of 60 Hz. FIG. 5b shows a curve 73 for the higher braking torque available with the present invention as compared with a curve 74 for dc braking as taught in the prior art for a 5 HP motor braked from a speed corresponding to a frequency of 90 Hz.

This has been a description of several preferred embodiments of the invention. It will be apparent that various modifications and details can be varied without departing from the scope and spirit of the invention, and these are intended to come within the scope of the following claims.

We claim:

1. A method of flux-reduced braking of an AC motor, comprising:
reducing commanded voltage while holding output frequency at a last running value to reduce flux in the motor;
upon reaching a flux-reduced level, reducing the output frequency by at least 40% and then sensing dc bus voltage to provide a feedback signal that regulates the frequency as a function of dc bus voltage to provide control of frequency down to about 3 Hz.; and
upon reaching the flux-reduced level, providing a motor current regulation loop to control the motor and providing with current commands to the motor current regulation loop that provide braking torque to the motor.

2. The method of claim 1, wherein dc current is applied to brake the motor upon sensing any one of the following conditions:
frequency command dropping below 3 Hz;
a frequency trend showing an increase instead of a decrease; and
the frequency command reaching a flux-reduced operating frequency.

3. The method of claim 1, wherein user-selectable parameters are provided by which the user can select a mode of braking from said flux-reduced braking, from dc braking and from a ramp-type braking.

4. The method of claim 1, wherein the frequency is reduced from the last running value by an amount in a range from 40% to 57%.

5. The method of claim 1, wherein a running speed is above base speed.

6. The method of claim 1, wherein a speed of the motor is decreased to zero along an increasingly downward sloping curve.

7. A controller for flux-reduced braking of an AC motor, comprising:
a microelectronic CPU for executing a stored control program to provide a dc bus voltage regulator that receives a dc reference voltage and a dc feedback voltage and for generating an output frequency in response thereto that controls an operating frequency of the AC motor;
the microelectronic CPU also providing a current regulator that receives current feedback responsive to current supplied to the motor and which controls a PWM inverter that supplies current to the motor; and
wherein the microelectronic CPU is responsive to program instructions in the stored control program to reduce commanded voltage while holding output frequency at a last running value to reduce flux in the motor;
upon reaching a flux-reduced level, reducing the output frequency by at least 40% and then sensing dc bus voltage to provide a feedback signal that regulates the output frequency as a function of dc bus voltage to provide control of the output frequency down to about 3 Hz.; and
upon reaching a flux-reduced level, the microelectronic CPU providing current commands to the motor current regulation loop to provide braking torque to the motor.

8. The controller of claim 7, wherein dc current is applied to brake the motor upon sensing any one of the following conditions:
an output frequency command dropping below 3 Hz;
a frequency trend showing an increase instead of a decrease; and
the output frequency command reaching the flux-reduced operating frequency.

9. The controller of claim 7, wherein user-selectable parameters are provided by which the user can select a mode of braking from said flux-reduced braking, from dc braking and from a ramp-type braking.

10. The controller of claim 7, wherein the output frequency is reduced from the last running value by an amount in the range from 40% to 57%.

11. The controller of claim 7, wherein a running speed of the motor is above base speed.

12. The controller of claim 7, wherein a running speed of the motor is decreased to zero along an increasingly downward sloping curve.

13. A method of flux-reduced braking of an AC motor, comprising:
reducing commanded voltage while holding output frequency at a last running value to reduce flux in the motor; and
upon reaching a flux-reduced level:
reducing the output frequency by a percentage;

sensing dc bus voltage to provide a feedback signal; and regulating the output frequency as a function of the dc bus voltage feedback signal to provide control of the output frequency down to a reduced value.

14. The controller of claim 13 further including the steps of, upon reaching the flux-reduced level:

providing a motor current regulation loop to control the motor; and providing current commands to the motor current regulation loop that provide braking torque to the motor.

15. The method of claim 13 wherein dc current is applied to brake the motor upon sensing any one of the following conditions:

an output frequency command dropping below the reduced value;

a frequency trend showing an increase instead of a decrease; and the output frequency command reaching a flux-reduced operating frequency.

16. The method of claim 13, wherein user-selectable parameters are provided by which the user can select a mode of braking from said flux-reduced braking, from dc braking and from a ramp-type braking.

17. The method of claim 13, wherein the output frequency is reduced from the last running value by a percentage in a range from 40% to 57%.

18. The method of claim 13 wherein the reduced value is 3 Hz.

19. A controller for flux-reduced braking of an AC motor, comprising:

a processor for executing a stored control program to provide a dc bus voltage regulator that receives a dc reference voltage and a dc feedback voltage and for generating an output frequency in response thereto that controls an operating frequency of the AC motor; and wherein the processor is responsive to program instructions in the stored control program to:

reduce commanded voltage while holding output frequency at a last running value to reduce flux in the motor;

upon reaching a flux-reduced level, reduce the output frequency by a percentage;

sense dc bus voltage to provide a feedback signal; and regulate the output frequency as a function of dc bus voltage to provide control of the output frequency down to a reduced value.

20. The controller of claim 19 further including a processor providing a current regulator that receives current feedback responsive to current supplied to the motor and which controls a PWM inverter that supplies current to the motor, the processor further responsive to program instructions in the stored control program to:

upon reaching the flux-reduced level, provide current commands to the motor current regulation loop to provide braking torque to the motor.

21. The controller of claim 19, wherein dc current is applied to brake the motor upon sensing any one of the following conditions:

an output frequency command dropping below the reduced value;

a frequency trend showing an increase instead of a decrease; and the output frequency command reaching the flux-reduced operating frequency.

22. The controller of claim 19, wherein the output frequency is reduced from the last running value by an amount in the range from 40% to 57%.

23. The controller of claim 19 wherein the reduced value is 3 Hz.

* * * * *